United States Patent
Graff et al.

(10) Patent No.: US 6,458,854 B2
(45) Date of Patent: Oct. 1, 2002

(54) PHOSPHOLIPIDS OF HYDROXYEICOSATETRAENOIC ACID-LIKE DERIVATIVES AND METHODS OF USE

(75) Inventors: Gustav Graff, Cleburne, TX (US); Peter G. Klimko, Fort Worth, TX (US)

(73) Assignee: Alcon Universal Ltd., Hunenberg (CH)

( * ) Notice: Subject to any disclaimer, the term of this patent is extended or adjusted under 35 U.S.C. 154(b) by 0 days.

(21) Appl. No.: 09/874,815

(22) Filed: Jun. 5, 2001

Related U.S. Application Data

(63) Continuation-in-part of application No. 09/694,138, filed on Oct. 23, 2000, now Pat. No. 6,353,032.
(60) Provisional application No. 60/164,367, filed on Nov. 9, 1999.

(51) Int. Cl.$^7$ ............................................. A01N 25/00
(52) U.S. Cl. ..................... 514/912; 514/572; 514/873; 514/914; 554/80
(58) Field of Search ......................... 514/912, 914, 514/572, 573; 554/80

(56) References Cited

U.S. PATENT DOCUMENTS

| | | | |
|---|---|---|---|
| 3,991,759 A | 11/1976 | Urquhart | 128/260 |
| 4,131,651 A | 12/1978 | Shah et al. | 424/78 |
| 4,370,325 A | 1/1983 | Packman | 424/245 |
| 4,409,205 A | 10/1983 | Shively | 424/78 |
| 4,421,748 A | 12/1983 | Trager et al. | 424/199 |
| 4,744,980 A | 5/1988 | Holly | 424/78 |
| 4,753,945 A | 6/1988 | Gilbard et al. | 514/263 |
| 4,804,539 A | 2/1989 | Guo et al. | 424/450 |
| 4,818,537 A | 4/1989 | Guo | 424/427 |
| 4,868,154 A | 9/1989 | Gilbard et al. | 514/13 |
| 4,883,658 A | 11/1989 | Holly | 424/80 |
| 4,906,467 A | 3/1990 | Schwartzman et al. | 424/80 |
| 4,914,088 A | 4/1990 | Glonek et al. | 514/76 |
| 4,921,644 A | 5/1990 | Lau et al. | 264/4.1 |
| 4,923,700 A | 5/1990 | Kaufman | 424/427 |
| 4,966,773 A | 10/1990 | Gressel et al. | 424/489 |
| 5,041,434 A | 8/1991 | Lubkin | 514/182 |
| 5,064,655 A | 11/1991 | Uster et al. | 424/450 |
| 5,075,104 A | 12/1991 | Gressel et al. | 424/78.04 |
| 5,174,988 A | 12/1992 | Mautone et al. | 424/45 |
| 5,278,151 A | 1/1994 | Korb et al. | 514/76 |
| 5,290,572 A | 3/1994 | MacKeen | 424/602 |
| 5,294,607 A | 3/1994 | Glonek et al. | 514/76 |
| 5,306,483 A | 4/1994 | Mautone | 424/45 |
| 5,358,706 A | 10/1994 | Marlin et al. | 424/78.04 |
| 5,371,108 A | 12/1994 | Korb et al. | 514/762 |
| 5,389,383 A | 2/1995 | Huth | 424/650 |
| 5,403,598 A | 4/1995 | Beck et al. | 424/717 |
| 5,403,841 A | 4/1995 | Lang et al. | 514/226.8 |
| 5,455,265 A | 10/1995 | Chandraratna | 514/448 |
| 5,578,586 A | 11/1996 | Glonek et al. | 514/76 |
| 5,620,921 A | 4/1997 | Sullivan | 514/178 |
| 5,696,166 A | 12/1997 | Yanni et al. | 514/573 |
| 5,800,807 A | 9/1998 | Hu et al. | 424/78.04 |
| 6,281,192 B1 | 8/2001 | Leahy et al. | 514/8 |

FOREIGN PATENT DOCUMENTS

| | | |
|---|---|---|
| CA | 1 251 736 | 3/1989 |
| EP | 0 097 059 A2 | 12/1983 |
| EP | 0 132 089 A1 | 1/1985 |
| WO | WO 91/12808 | 9/1991 |
| WO | WO 92/04905 | 4/1992 |
| WO | WO 98/16240 | 4/1998 |

OTHER PUBLICATIONS

Alpert et al., "Human Tracheal Epithelial Cells Selectively Incorporate 15–Hydroxyeicosatetraenoic Acid into Phosphatidylinositol," *Am. J. Respir. Cell Mol. Biol.*, vol. 8, pp. 273–281 (1993).

Baba et al., "Chemoenzymatic Synthesis of Phosphatidyl–L–serine Hydroperoxide," *Biosci. Biotech. Biochem.*, vol. 58(10), pp. 1927–1928 (1994).

Brash et al., "Analysis of a Specific Oxygenation Reaction of Soybean Lipoxygenase–1 with Fatty Acids Esterified in Phospholipids," *Biochemistry*, vol. 26(17), pp. 5465–5471 (1987).

Corfield et al., "Ocular Mucins: Purification, Metabolism and Functions," *Prog Retinal Eye Res.*, vol. 16, pp. 627–656 (1997).

Danjo et al., "Alteration of Mucin in Human Conjunctival Epithelia in Dry Eye," *Invest Ophthalmol Vis. Sci.*, vol. 39; pp. 2602–2609 (1998).

Dartt et. al., Vasoactive intestinal peptide–stimulated glycocongjugate secretion from conjunctival goblet cells. Experimental Eye Research, vol. 63, pp. 27–34, (1996).

Dilly et al., "Surface Changes in the Anesthetic Conjunctiva in Man, with Special Reference to the Production of Mucus from a Non–Goblet–Cell Source," *British Journal of Ophthalmology*, vol. 65; pp. 833–842 (1981).

Dohlman, "Symposium on the Dry Eye, New Concepts in Ocular Xerosis," *Ophthalmological Societies of the United Kingdom*, vol. XCI; pp. 105–118 (1971).

Glasglow et al. ,"Tear lipocalins bind a broad array of lipid ligands," *Current Eye Research*, vol. 14(5), pp. 363–372 (1995).

Graber et al., 15–Hydroxyeicosatetraenoic Acid Stimulates Migration of Human Retinal Microvessel Endothelium In Vitro and Neovascularization In Vivo, *Prostaglandins*, vol. 39 (6); pp. 665–673 (1990).

Greiner et al., "Histochemical Analysis of Secretory Vesicles in Non–Goblet Conjunctival Epithelial Cells," *Acta Ophthalmol.*, vol. 63; pp. 89–92 (1985).

Greiner et al., Meibomian gland phospholipids, *Current Eye Research*, vol. 15(4); pp. 371–375 (1996).

(List continued on next page.)

*Primary Examiner*—Deborah D. Carr
(74) *Attorney, Agent, or Firm*—Patrick M. Ryan

(57) ABSTRACT

Phospholipid-HETE derivatives, compositions and methods of use are disclosed. The compounds are particularly useful for treating dry eye.

8 Claims, No Drawings

OTHER PUBLICATIONS

Greiner et al., "Mucus Secretory Vesicles in Conjunctival Epithelial Cells of Wearers of Contact Lenses," *Arch Ophthalmol.*, vol. 98; pp. 1843–1846 (1980).

Greiner et al., "Phospholipids in Meibomian Gland Secretion," *Ophthalmic Res.*, vol. 28, pp. 44–49 (1996).

Hamberg et al., "Identification of 15–hydroxy–5.8.11.13–eicosatetraenoic acid (15–HETE) as a major metabolite of arachidonic acid in human lung," *Acta Physiol Scand.*, vol. 110; pp. 219–221 (1980).

Holly et al., "Tear Physiology and Dry Eyes," *Surv. Ophthalmol.*, vol. 22; pp. 69–87 (1977).

Holzfeind et al., "The Human Lacrimal Gland Synthesizes Apolipoprotein D mRNA in Addition to Tear Prealbumin mRNA, Both Species Encoding Members of the Lipocalin Superfamily," *Exp. Eye Res.*, vol. 65, pp. 495–500 (1995).

Hutchinson, "Arachidonate 15–lipoxygenase; characteristics and potential biological significance," *Eicosanoids*, vol. 4, pp. 65–74 (1991).

Inatomi et al., "Human Corneal and Conjunctival Epithelia Express MUC1 Mucin," *Invest Ophthalmol Vis Sci.*, vol. 36; pp. 1818–1827 (1995).

Isaacson et al., "The Synthesis and Molecular Dynamics of Phospholipids Having Hydroxylated Fatty Acids at the sn–2 position," *Chemistry and Physics of Lipids*, vol. 52, pp. 217–226 (1990).

Jansen et al., "Phospholipids Chiral at Phosphorus. Synthesis and Stereospecificity of Phosphorothioate Analogues of Platelet–Activating Factor," *Biochemistry*, vol. 27, pp. 4619–4624 (1988).

Johnson et al., 15–Hydroxyeicosatetraenoic Acid is a Potent Inflammatory Mediator and Agonist of Canine Tracheal Mucus Secretion, from the Hypersensitivity Diseases Research, Lipids Research. The Upjohn Company, Kalamazoo, Michigan, pp. 917–922 (1984).

Kessing et al., "Mucous Gland System of the Conjunctiva," *Acta Ophthalmol. Suppl.*, vol. 95; pp. 1–133 (1968).

Korb et al., Tear Film Lipid Layer Formation: Implications for Contact Lens Wear, *Optometry and Vision Science*, vol. 73(3), pp. 189–192 (1996).

Legrand et al., "Substitution of 15–Hydroxyeicosatetraenoic Acid in the Phosphoinositide Signaling Pathway," *J. of Biological Chemistry*, vol. 266 (12), pp. 7570–7577 (1991).

Lemp et al., "Report of the National Eye Institute/Industry Workshop on Clinical Trials is Dry Eyes," *CLAO*, vol. 21(4), pp. 221–231 (1995).

Lemp, "Tear Substitutes in the Treatment of Dry Eyes," *External Ocular Diseases: Diagnosis and Current Therapy*, Laibson and Trobe (ed.) Little, Brown and Company, Boston; vol. 13(4); pp. 145–153 (1973).

Marom et al., "Effects of Arachidonic Acid, Monohydroxyeicosatetraenoic Acid and Prostaglandins on the Release of Mucous Glycoproteins from Human Airways In Vitro," *The J. of Clinical Investigation*, vol. 67; pp. 1695–1702 (1981).

Marom et al., "Human Airway Monohydroxyeicosatetraenoic Acid Generation and Mucus Release," *Journal of Clinical Investigation*, vol. 72, pp. 122–127 (1983).

Masferrer et al., "12(R)–Hydroxyeicosatetraenoic Acid, An Endogenous corneal Arachidonate Metabolite, Lowers Intraocular Pressure in Rabbits," *Investigative Ophthalmology and Visual Science*, vol. 31(3); pp. 535–539 (1990).

McCulley et al., "Tear Film Structure and Dry Eye," *Contactologia*, vol. 20, pp. 145–149 (1998).

Mysore et al., "Controlled Ocular Drug Delivery and Vesicular Systems: An Overview," *Indian Drugs*, vol. 33(9), pp. 431–442 (1996).

Nakamura et al., "Gefarnate stimulates secretion of mucin–like glycoproteins by corneal epithelium in vitro and protects corneal epithelium from dessication in vivo," *Experimental Eye Research*, vol. 65, pp. 569–574 (1997).

Ohno, M.; Otsuka, M. Organic Reactions, vol. 37, Chapter 1, pp. 1–55 (1989).

Ohyama et al., "Sensitive Densitometry for the Determination of Platelet–activating Factor and Other Phospholipids in Human Tears," *Analyst*, vol. 121, pp. 1943–1947 (1996).

Pleyer et al., "Analysis of Interactions Between the Corneal Epithelium and Liposomes" Qualitative and Quantitative Fluorescence Studies of a Corneal Epithelial Cell Line, *Survey of Ophthalmology*, vol. 39 (Supl. 1), S3–S16 (1995).

Profita et al., "Interleukin–4 Enhances 15–Lipoxygenase Activity and Incorporation of 15(S)–HETE into Cellular Phospholipids in Cultured Pulmonary Epithelial Cells," *Am. J. Respir. Cell Mol. Biol.*, vol. 20, pp. 61–68 (1999).

Prydal et al., "Study of Human Tear Film Thickness and Structure Using Laser Interferometry," *Invest Ophthalmol Vis Sci.*, vol. 33; pp. 2006–2011 (1992).

Shelhamer et al., "The Effects of Arachinoids and Leukotrienes on the Release of Mucus from Human Airways," *Chest Supplement*, $24^{th}$ Aspen Lung Conference, vol. 81(5); pp. 36S–37S (1982).

Shigemitsu et al., "Effects of Mucin Ophthalmic Solution on Epithelial Wound Healing in Rabbit Cornea," *Ophthalmic Res.*, vol. 29; pp. 61–66 (1997).

Shine et al., Keratoconjunctivitis Sicca Associated with Meibomian Secretion Polar Lipid Abnormality, *Arch. Ophthalmology*, vol. 116, pp. 849–852 (1998).

Watanabe et al., "Human Corneal and Conjunctival Epithelia Produce a Mucin–like Glycoprotein for the Apical Surface," *Invest Ophthalmol Vis Sci.*, vol. 36; pp. 337–344 (1995).

Wiggins et al., "12(S)–Hydroxy–5,8.10.14–Eicosatetraenoic Acid is a More Potent Neutrophil Chemoattractant Than the 12(R) Epimer in the Rat Cornea," *Prostaglandins*, vol. 49(2) pp. 131–141 (1990).

Yanni et al., "Effect of Intravenously Administered Lipoxygenase Metabolites on Rat Tracheal Mucous Gel Layer Thickness," *Int Arch Allergy Appl Immunol*, vol. 90 pp. 307–309 (1989).

Yu et al., "Effect of Polar Head Groups on the Interactions of Phospholipase $A_2$ with Phosphonate Transition–State Analogues," *Biochemistry*, vol. 32, pp. 10185–10192.

Zhang et al., "Enzymatic Asymmetric Hydroxylation of Pentadienols Using Soybean Lipoxygenase," *J. Am. Chem. Soc.*, vol. 111(26), pp. 9241–9242 (1989).

Zhu et al., Synthesis of Phospholipids Bearing a Conjugated Oxo–polyunsaturated Fatty Acid Residue, *J. Chem. Research* (S)., vol. 8, pp. 500–501 (1999).

PHOSPHOLIPIDS OF HYDROXYEICOSATETRAENOIC ACID-LIKE DERIVATIVES AND METHODS OF USE

This application is a continuation-in-part application of U.S. Ser. No. 09/694,138, filed Oct. 23, 2000, now U.S. Pat. No. 6,353,032, which claims priority to U.S. Provisional Application, U.S. Ser. No. 60/164,367 filed Nov. 9, 1999. The present invention is directed to compositions containing phospholipids comprised of hydroxyeicosatetraenoic acid derivatives and methods of use in treating dry eye.

BACKGROUND OF THE INVENTION

Dry eye, also known generically as keratoconjunctivitis sicca, is a common ophthalmological disorder affecting millions of Americans each year. The condition is particularly widespread among post-menopausal women due to hormonal changes following the cessation of fertility. Dry eye may afflict an individual with varying severity. In mild cases, a patient may experience burning, a feeling of dryness, and persistent irritation such as is often caused by small bodies lodging between the eye lid and the eye surface. In severe cases, vision may be substantially impaired. Other diseases, such as Sjogren's disease and cicatricial pemphigoid manifest dry eye complications.

Although it appears that dry eye may result from a number of unrelated pathogenic causes, all presentations of the complication share a common effect, that is the breakdown of the pre-ocular tear film, which results in dehydration of the exposed outer surface and many of the symptoms outlined above (Lemp, *Report of the National Eye Institute/Industry Workshop on Clinical Trials in Dry Eyes, The CLAO Journal,* volume 21, number 4, pages 221–231 (1995)).

Practitioners have taken several approaches to the treatment of dry eye. One common approach has been to supplement and stabilize the ocular tear film using so-called artificial tears instilled throughout the day. Other approaches include the use of ocular inserts that provide a tear substitute or stimulation of endogenous tear production.

Examples of the tear substitution approach include the use of buffered, isotonic saline solutions, aqueous solutions containing water soluble polymers that render the solutions more viscous and thus less easily shed by the eye. Tear reconstitution is also attempted by providing one or more components of the tear film such as phospholipids and oils. Phospholipid compositions have been shown to be useful in treating dry eye; see, e.g., McCulley and Shine, *Tear film structure and dry eye. Contactologia,* volume 20(4), pages 145–49 (1998); and Shine and McCulley, *Keratoconjunctivitis sicca associated with meibomian secretion polar lipid abnormality, Archives of Ophthalmology,* volume 116(7), pages 849–52 (1998). Examples of phospholipid compositions for the treatment of dry eye are disclosed in U.S. Pat. No. 4,131,651 (Shah et al.), U.S. Pat. No. 4,370,325 (Packman), U.S. Pat. No. 4,409,205 (Shively), U.S. Pat. No. 4,744,980 and U.S. Pat. No. 4,883,658 (Holly), U.S. Pat. No. 4,914,088 (Glonek), U.S. Pat. No. 5,075,104 (Gressel et al.), U.S. Pat. No. 5,278,151 (Korb et al.), U.S. Pat. No. 5,294,607 (Glonek et al.), U.S. Pat. No. 5,371,108 (Korb et al.) and U.S. Pat. No. 5,578,586 (Glonek et al.). U.S. Pat. No. 5,174,988 (Mautone et al.) discloses phospholipid drug delivery systems involving phospholipids, propellants and an active substance.

U.S. Pat. No. 3,991,759 (Urquhart) discloses the use of ocular inserts in the treatment of dry eye. Other semi-solid therapy has included the administration of carrageenans (U.S. Pat. No. 5,403,841, Lang) which gel upon contact with naturally occurring tear film.

Another approach involves the provision of lubricating substances in lieu of artificial tears. For example, U.S. Pat. No. 4,818,537 (Guo) discloses the use of a lubricating, liposome-based composition, and U.S. Pat. No. 5,800,807 (Hu et al.) discloses compositions containing glycerin and propylene glycol for treating dry eye.

Aside from the above efforts, which are directed primarily to the alleviation of symptoms associated with dry eye, methods and compositions directed to treatment of the dry eye condition have also been pursued. For example, U.S. Pat. No. 5,041,434 (Lubkin) discloses the use of sex steroids, such as conjugated estrogens, to treat dry eye condition in post-menopausal women; U.S. Pat. No. 5,290,572 (MacKeen) discloses the use of finely divided calcium ion compositions to stimulate pre-ocular tear film production; and U.S. Pat. No. 4,966,773 (Gressel et al.) discloses the use of microfine particles of one or more retinoids for ocular tissue normalization.

Although these approaches have met with some success, problems in the treatment of dry eye nevertheless remain. The use of tear substitutes, while temporarily effective, generally requires repeated application over the course of a patient's waking hours. It is not uncommon for a patient to have to apply artificial tear solution ten to twenty times over the course of the day. Such an undertaking is not only cumbersome and time consuming, but is also potentially very expensive. Transient symptoms of dry eye associated with refractive surgery have been reported to last in some cases from six weeks to six months or more following surgery.

The use of ocular inserts is also problematic. Aside from cost, they are often unwieldy and uncomfortable. Further, as foreign bodies introduced in the eye, they can be a source of contamination leading to infections. In situations where the insert does not itself produce and deliver a tear film, artificial tears must still be delivered on a regular and frequent basis.

In view of the foregoing, there is a clear need for an effective, convenient treatment for dry eye that is capable of alleviating symptoms, as well as treating the underlying physical and physiological deficiencies of dry eye.

Mucins are proteins which are heavily glycosylated with glucosamine-based moieties. Mucins provide protective and lubricating effects to epithelial cells, especially those of mucosal membranes. Mucins have been shown to be secreted by vesicles and discharged on the surface of the conjunctival epithelium of human eyes (Greiner et al., *Mucous Secretory Vesicles in Conjunctival Epithelial Cells of Wearers of Contact Lenses, Archives of Ophthalmology,* volume 98, pages 1843–1846 (1980); and Dilly et al., *Surface Changes in the Anaesthetic Conjunctiva in Man, with Special Reference to the Production of Mucous from a Non-Goblet-Cell Source, British Journal of Ophthalmology,* volume 65, pages 833–842 (1981)). A number of human-derived mucins which reside in the apical and subapical corneal epithelium have been discovered and cloned (Watanabe et al., *Human Corneal and Conjunctival Epithelia Produce a Mucin-Like Glycoprotein for the Apical Surface, Investigative Ophthalmology and Visual Science,* volume 36, number 2, pages 337–344 (1995)). Recently, Watanabe discovered a new mucin which is secreted via the cornea apical and subapical cells as well as the conjunctival epithelium of the human eye (Watanabe et al., IOVS, volume 36, number 2, pages 337–344 (1995)). These mucins provide lubrication, and additionally attract and hold moisture and sebaceous material for lubrication and the corneal refraction of light.

Mucins are also produced and secreted in other parts of the body including lung airway passages, and more specifically from goblet cells interspersed among tracheal/bronchial epithelial cells. Certain arachidonic acid metabolites have been shown to stimulate mucin production in these cells. Yanni reported the increased secretion of mucosal glycoproteins in rat lung by hydroxyeicosatetraenoic acid ("HETE") derivatives (Yanni et al, *Effect of Intravenously Administered Lipoxygenase Metabolites on Rat Trachael Mucous Gel Layer Thickness, International Archives of Allergy And Applied Immunology,* volume 90, pages 307–309 (1989)). Similarly, Marom has reported the production of mucosal glycoproteins in human lung by HETE derivatives (Marom et al., *Human Airway Monohydroxyeicosatetraenoic Acid Generation and Mucous Release, Journal of Clinical Investigation,* volume 72, pages 122–127 (1983)).

Agents claimed for increasing ocular mucin and/or tear production include vasoactive intestinal polypeptide (Dartt et. al., *Vasoactive intestinal peptide-stimulated glycoconjiugate secretion from conjunctival goblet cells. Experimental Eye Research,* volume 63, pages 27–34, (1996)), gefarnate (Nakmura et. al., *Gefarnate stimulates secretion of mucin-like glycoproteins by corneal epithelium in vitro and protects corneal epithelium from dessication in vivo, Experimental Eye Research,* volume 65, pages 569–574 (1997)), liposomes (U.S. Pat. No. 4,818,537), androgens (U.S. Pat. No. 5,620,921), melanocycte stimulating hormones (U.S. Pat. No. 4,868,154), phosphodiesterase inhibitors (U.S. Pat. No. 4,753,945), and retinoids (U.S. Pat. No. 5,455,265). However, many of these compounds or treatments suffer from a lack of specificity, efficacy and potency and none of these agents have been marketed so far as therapeutically useful products to treat dry eye and related ocular surface diseases.

U.S. Pat. No. 5,696,166 (Yanni et al.) discloses compositions containing HETE derivatives and methods of use for treating dry eye. Yanni et al. discovered that compositions comprising HETE derivatives increase ocular mucin secretion and are thus useful in treating dry eye. Such compositions, however, only act to increase ocular mucin secretion, leading to the rebuilding of the natural tears. While such compositions are therapeutically useful in treating an underlying cause of dry eye, such compositions may not immediately alleviate the symptoms of dry eye following administration. The inventors of the present invention have invented improved HETE-related molecules and compositions which provide both immediate, as well as long-term, dry eye relief.

HETEs have been shown to incorporate in phospholipids in cell cultures. See, e.g., *Substitution of 15-Hydroxyeicosatetraenoic Acid in the Phosphoinositide Signaling Pathway, Journal of Biological Chemistry,* volume 266, No. 12, pages 7570–7571 (1991); *Human Tracheal Epithelial Cells Selectively Incorporate 15-Hydroxyeicosatetraenoic Acid into Phosphatidylinositol, Am. J. Respir. Cell Mol. Biol.,* volume 8, pages 273–281 (1993); and *Interleukin-4 Enhances 15-Lipoxygenase Activity and Incorporation of 15(S)-HETE into Cellular Phospholipids in Cultured Pulmonary Epithelial Cells, Am. J. Respir. Cell Mol. Biol.,* volume 20, pages 61–68 (1999). Changjin et al. disclose the synthesis of a phospholipid containing 15-keto-HETE (*Synthesis of Phospholipids Bearing a Conjugated Oxo-polyunsaturated Fatty Acid Residue,* *J. Che. Res. Synop.,* volume 8, pages 500–501 (1999)). Nowhere in the art, however, have pharmaceutical compositions comprising HETE derivative-containing phospholipids and methods of use for the treatment of dry eye been disclosed or taught.

SUMMARY OF THE INVENTION

The present invention is directed to novel phospholipid-HETE derivative compounds, compositions and methods of use. Preferred methods are directed to the treatment of dry eye-type diseases and disorders requiring the wetting of the eye, including symptoms of dry eye associated with refractive surgery such as LASIK surgery. The compositions are preferably administered topically to the eye.

The compositions and methods of the present invention provide the advantages of a two-part system for treating dry eye-type diseases and disorders. The phospholipid-HETE derivatives may act as a pro-drug wherein the HETE derivative is cleaved from the phospholipid in vivo following topical administration to the eye. The released HETE derivative may then act to stimulate mucin production while the free phospholipid may concurrently provide for immediate wetting, tear build-up, lubrication or otherwise improving the dry eye condition of the eye due to its amphipathic and humectant characteristics. Additionally, the use of phospholipid-HETE derivative pro-drugs may enhance the stability of the HETE derivative in its pharmaceutical composition. Since the instability of HETE derivatives may be linked to their free terminal carboxylate in an aqueous environment, "tying off" the HETE derivative carboxylate by covalent attachment to the phospholipid backbone may improve the stability of the HETE-containing compositions.

The phospholipid-HETE derivatives of the present invention may also act to stimulate mucin production and concurrently provide for the wetting, tear build-up or lubrication of the eye without the need for cleavage of the HETE from the glycerol backbone.

DETAILED DESCRIPTION OF THE INVENTION

The present invention is directed to phospholipids comprising HETE derivatives and methods of use in treating dry eye-type diseases and disorders. It is believed that the phospholipid-HETE derivatives stimulate ocular mucin production and/or secretion following topical ocular application, and also provide for the wetting, tear build-up or lubrication of the eye, either as the phospholipid-HETE complex or as the cleaved, individual phospholipid and HETE components following topical application to the eye. The phospholipid-HETE derivatives of the present invention are of formula I:

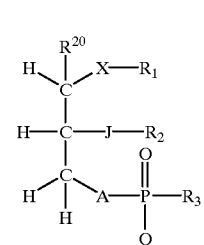

(I)

wherein:

$R^{20}$ is H or Ch=CH(CH$_2$)$_{12}$CH$_3$;

X is O or S;

$R^1$ is H, (C=O)$R^4$ or $CH_2R^4$;

J is O or NH;

$R^2$ is (C=O)$R^5$;

A is $CH_2$ or O;

$R^3$ is $OCH_2CH(NH_3^+)COO^-$, $OCH_2CH_2NH_3+$, $OCH_2CH_2N^+(CH_3)_3$, $OCH_2CH(OH)CH_2OH$, O-inositol, OH, H, or alkyl;

$R^4$ and $R^5$ are independently a HETE derivative; substituted or unsubstituted $C_{12-30}$ alkyl or alkenyl (the alkenyl group containing one or more double bonds); alkyl(cycloalkyl)alkyl; alkyl(cycloalkyl); alkyl (heteroaryl); alkyl(heteroaryl)alkyl; or alkyl-M-Q; wherein the substitution is alkyl, halo, hydroxy, or functionally modified hydroxy; wherein:

M is O or S; and

Q is H, alkyl, alkyl(cycloalkyl)alkyl, alkyl(cycloalkyl), alkyl(heteroaryl) or alkyl(heteroaryl)alkyl;

with the proviso that at least one of $R^4$ and $R^5$ must be a HETE derivative;

wherein HETE derivative is a structural fragment of formula II:

II:

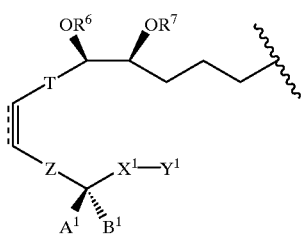

wherein:

$OR^6$ and $OR^7$ are the same or different and comprise a free or functionally modified hydroxy group;

T and Z are the same or different and are $CH_2CH_2$, cis- or trans-CH=CH or C≡C;

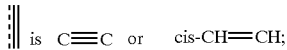

one of $A^1$, $B^1$ is H or $CH_3$, and the other is a free or functionally modified hydroxy group, or $A^1$-$B^1$ comprises a double bonded oxygen as a carbonyl, or $A^1$-$B^1$ is $OCH_2CH_2O$;

$X^1$ is $CR^{16}R^{17}(CH_2)_q$ or $CR^{16}R^{17}(CH_2)_qO$, with q is 0–6; $R^{16}$ and $R^{17}$ are the same or different and are H or $CH_3$;

$Y^1$ is $CH_3$, or a phenyl ring optionally substituted with alkyl, halo, trihalomethyl, acyl, or a free or functionally modified hydroxy, thiol, or amino group;

or $X^1$-$Y^1$ is $(CH_2)_pY^{20}$, p is 0–6,

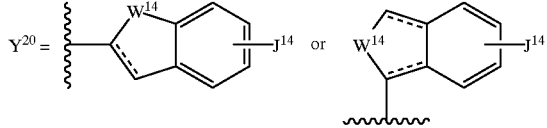

wherein:

$W^{14}$ is $CH_2$, O, S(O)$_m$, $NR^{21}$, $CH_2CH_2$, Ch=CH, $CH_2O$, $CH_2S(O)_m$, Ch=N, or $CH_2NR^{21}$;

m is 0–2;

$NR^{21}$ is NH or a functionally modified amino group;

$J^{14}$ is H, alkyl, acyl, halo, trihalomethyl, or a free or functionalized hydroxy, thiol, or amino group; and — is a single or double bond;

or $X^1$-$Y^1$ is cyclohexyl; and the wavy line indicates the point of attachment.

It is believed that all of compounds of formula (I) are novel.

Included within the scope of the present invention are the individual enantiomers of the formula (I) compounds, as well as their racemic and non-racemic mixtures. The individual enantiomers can be enantioselectively synthesized from the appropriate enantiomerically pure or enriched starting material by means such as those described below. Alternatively, they may be enantioselectively synthesized from racemic/non-racemic or achiral starting materials. (*Asymmetric Synthesis;* J. D. Morrison and J. W. Scott, Eds.; Academic Press Publishers: New York, 1983–1985, volumes 1–5; *Principles of Asymmetric Synthesis;* R. E. Gawley and J. Aube, Eds.; Elsevier Publishers: Amsterdam, 1996). They may also be isolated from racemic and non-racemic mixtures by a number of known methods, e.g. by purification of a sample by chiral HPLC (*A Practical Guide to Chiral Separations by HPLC;* G. Subramanian, Ed.; VCH Publishers: New York, 1994; *Chiral Separations by HPLC;* A. M. Krstulovic, Ed.; Ellis Horwood Ltd. Publishers, 1989), or by enantioselective hydrolysis of a carboxylic acid ester sample by an enzyme (Ohno, M.; Otsuka, M. *Organic Reactions,* volume 37, page 1 (1989)). Those skilled in the art will appreciate that racemic and non-racemic mixtures may be obtained by several means, including without limitation, nonenantioselective synthesis, partial resolution, or even mixing samples having different enantiomeric ratios. Departures may be made from such details within the scope of the accompanying claims without departing from the principles of the invention and without sacrificing its advantages. Also included within the scope of the present invention are the individual isomers substantially free of their respective enantiomers.

As used herein, wavy line attachments indicate that the configuration may be either alpha (α) or beta (β). Hatched lines indicate the α configuration. A solid triangular line indicates the β configuration.

As used herein, the terms "pharmaceutically acceptable salt", "pharmaceutically acceptable ester" and "pharmaceutically acceptable thioester" means any salt, ester or thioester, respectively, that would be suitable for therapeutic administration to a patient by any conventional means without significant deleterious health consequences; and "ophthalmically acceptable salt", "ophthalmically acceptable ester" and "ophthalmically acceptable thioester" means any pharmaceutically acceptable salt, ester or thioester, respectively, that would be suitable for ophthalmic application, i.e. non-toxic and non-irritating.

The term "free hydroxy group" means an OH. The term "functionally modified hydroxy group" means an OH which has been functionalized to form: an ether, in which an alkyl, aryl, cycloalkyl, heterocycloalkyl, alkenyl, cycloalkenyl, heterocycloalkenyl, alkynyl, or heteroaryl group is substituted for the hydrogen; an ester, in which an acyl group is substituted for the hydrogen; a carbamate, in which an aminocarbonyl group is substituted for the hydrogen; or a carbonate, in which an aryloxy-, heteroaryloxy-, alkoxy-, cycloalkoxy-, heterocycloalkoxy-, alkenyloxy-, cycloalkenyloxy-, heterocycloalkenyloxy-, or alkynyloxy-carbonyl group is substituted for the hydrogen. Preferred moieties include OH, $OCH_2C(O)CH_3$, $OCH_2C(O)C_2H_5$, $OCH_3$, $OCH_2CH_3$, $OC(O)CH_3$, and $OC(O)C_2H_5$.

The term "free amino group" means an $NH_2$. The term "functionally modified amino group" means an $NH_2$ which has been functionalized to form: an aryloxy-, heteroaryloxy-, alkoxy-, cycloalkoxy-, heterocycloalkoxy-, alkenyl-, cycloalkenyl-, heterocycloalkenyl-, alkynyl-, or hydroxy-amino group, wherein the appropriate group is substituted for one of the hydrogens; an aryl-, heteroaryl-, alkyl-, cycloalkyl-, heterocycloalkyl-, alkenyl-, cycloalkenyl-, heterocycloalkenyl-, or alkynyl-amino group, wherein the appropriate group is substituted for one or both of the hydrogens; an amide, in which an acyl group is substituted for one of the hydrogens; a carbamate, in which an aryloxy-, heteroaryloxy-, alkoxy-, cycloalkoxy-, heterocycloalkoxy-, alkenyl-, cycloalkenyl-, heterocycloalkenyl-, or alkynyl-carbonyl group is substituted for one of the hydrogens; or a urea, in which an aminocarbonyl group is substituted for one of the hydrogens. Combinations of these substitution patterns, for example an $NH_2$ in which one of the hydrogens is replaced by an alkyl group and the other hydrogen is replaced by an alkoxycarbonyl group, also fall under the definition of a functionally modified amino group and are included within the scope of the present invention. Preferred moieties include $NH_2$, $NHCH_3$, $NHC_2H_5$, $N(CH_3)_2$, $NHC(O)CH_3$, $NHOH$, and $NH(OCH_3)$.

The term "free thiol group" means an SH. The term "functionally modified thiol group" means an SH which has been functionalized to form: a thioether, where an alkyl, aryl, cycloalkyl, heterocycloalkyl, alkenyl, cycloalkenyl, heterocycloalkenyl, alkynyl, or heteroaryl group is substituted for the hydrogen; or a thioester, in which an acyl group is substituted for the hydrogen. Preferred moieties include SH, $SC(O)CH_3$, $SCH_3$, $SC_2H_5$, $SCH_2C(O)C_2H_5$, and $SCH_2C(O)CH_3$.

The term "acyl" represents a group that is linked by a carbon atom that has a double bond to an oxygen atom and a single bond to another carbon atom.

The term "alkyl" includes straight or branched chain aliphatic hydrocarbon groups that are saturated and have 1 to 15 carbon atoms. The alkyl groups may be interrupted by one or more heteroatoms, such as oxygen, nitrogen, or sulfur, and may be substituted with other groups, such as halogen, hydroxyl, aryl, cycloalkyl, aryloxy, or alkoxy. Preferred straight or branched alkyl groups include methyl, ethyl, propyl, isopropyl, butyl and t-butyl.

The term "cycloalkyl" includes straight or branched chain, saturated or unsaturated aliphatic hydrocarbon groups which connect to form one or more rings, which can be fused or isolated. The rings may be substituted with other groups, such as halogen, hydroxyl, aryl, aryloxy, alkoxy, or lower alkyl. Preferred cycloalkyl groups include cyclopropyl, cyclobutyl, cyclopentyl and cyclohexyl.

The term "$C_1$–$C_5$ cyclopropyl" means an alkyl chain of 1 to 5 carbon atoms containing a cyclopropyl group wherein the cyclopropyl group may start, be contained in or terminate the alkyl chain.

The term "heterocycloalkyl" refers to cycloalkyl rings that contain at least one heteroatom such as O, S, or N in the ring, and can be fused or isolated. The rings may be substituted with other groups, such as halogen, hydroxyl, aryl, aryloxy, alkoxy, or lower alkyl. Preferred heterocycloalkyl groups include pyrrolidinyl, tetrahydrofuranyl, piperazinyl, and tetrahydropyranyl.

The term "alkenyl" includes straight or branched chain hydrocarbon groups having 1 to 15 carbon atoms with at least one carbon-carbon double bond, the chain being optionally interrupted by one or more heteroatoms. The chain hydrogens may be substituted with other groups, such as halogen. Preferred straight or branched alkenyl groups include, allyl, 1-butenyl, 1-methyl-2-propenyl and 4-pentenyl.

The term "cycloalkenyl" includes straight or branched chain, saturated or unsaturated aliphatic hydrocarbon groups which connect to form one or more non-aromatic rings containing a carbon-carbon double bond, which can be fused or isolated. The rings may be substituted with other groups, such as halogen, hydroxyl, alkoxy, or lower alkyl. Preferred cycloalkenyl groups include cyclopentenyl and cyclohexenyl.

The term "heterocycloalkenyl" refers to cycloalkenyl rings which contain one or more heteroatoms such as O, N, or S in the ring, and can be fused or isolated. The rings may be substituted with other groups, such as halogen, hydroxyl, aryl, aryloxy, alkoxy, or lower alkyl. Preferred heterocycloalkenyl groups include pyrrolidinyl, dihydropyranyl, and dihydrofuranyl.

The term "carbonyl group" represents a carbon atom double bonded to an oxygen atom, wherein the carbon atom has two free valencies.

The term "aminocarbonyl" represents a free or functionally modified amino group bonded from its nitrogen atom to the carbon atom of a carbonyl group, the carbonyl group itself being bonded to another atom through its carbon atom.

The term "lower alkyl" represents alkyl groups containing one to six carbons ($C_1$–$C_6$).

The term "halogen" represents fluoro, chloro, bromo, or iodo.

The term "aryl" refers to carbon-based rings which are aromatic. The rings may be isolated, such as phenyl, or fused, such as naphthyl. The ring hydrogens may be substituted with other groups, such as lower alkyl, halogen, free or functionalized hydroxy, trihalomethyl, etc. Preferred aryl groups include phenyl, 3-(trifluoromethyl)phenyl, 3-chlorophenyl, and 4-fluorophenyl.

The term "heteroaryl" refers to aromatic hydrocarbon rings which contain at least one heteroatom such as O, S, or N in the ring. Heteroaryl rings may be isolated, with 5 to 6 ring atoms, or fused, with 8 to 10 atoms. The heteroaryl ring(s) hydrogens or heteroatoms with open valency may be substituted with other groups, such as lower alkyl or halogen. Examples of heteroaryl groups include imidazole, pyridine, indole, quinoline, furan, thiophene, pyrrole, tetrahydroquinoline, dihydrobenzofuran, and dihydrobenzindole.

The terms "aryloxy", "heteroaryloxy", "alkoxy", "cycloalkoxy", "heterocycloalkoxy", "alkenyloxy", "cycloalkenyloxy", "heterocycloalkenyloxy", and "alkynyloxy" represent an aryl, heteroaryl, alkyl, cycloalkyl, heterocycloalkyl, alkenyl, cycloalkenyl, heterocycloalkenyl, or alkynyl group, respectively, attached through an oxygen linkage.

The terms "alkoxycarbonyl", "aryloxycarbonyl", "heteroaryloxycarbonyl", "cycloalkoxycarbonyl", "heterocycloalkoxycarbonyl", "alkenyloxycarbonyl", "cycloalkenyloxycarbonyl", "heterocycloalkenyloxycarbonyl", and "alkynyloxycarbonyl" represent an alkoxy, aryloxy, heteroaryloxy, cycloalkoxy, heterocycloalkoxy, alkenyloxy, cycloalkenyloxy, heterocycloalkenyloxy, or alkynyloxy group, respectively, bonded from its oxygen atom to the carbon of a carbonyl group, the carbonyl group itself being bonded to another atom through its carbon atom.

Preferred compounds of the present invention include those of formula I, wherein:

X is O;

$R^1$ is H or (C=O)$R^4$;

A is O;

$R^3$ is $OCH_2CH(NH_3^+)COO^-$, $OCH_2CH_2NH_3+$, $OCH_2CH_2N^+(CH_3)_3$, O-inositol, or OH; and $R^5$ is a HETE derivative.

The compounds of formula (I) may be made by methods known in the art of phospholipid synthesis.

The compositions of the present invention comprise one or more compounds of formula (I) and a pharmaceutically acceptable carrier. The compositions are formulated in accordance with methods known in the art for the particular route of administration desired for the prevention, treatment or amelioration of the particular disease or disorder targeted. The level of peroxy compounds in the HETE derivative raw materials that are used to prepare the pharmaceutical formulations of the present invention may have an impact on the HETE derivative's biological activity. Although the precise relationship has not been defined, it is preferable to use HETE derivative raw material supplies containing peroxy compounds at levels no greater than about 0.3 ppm. Methods for determining peroxy levels are known in the art (e.g., European Pharmacopoeia 1997 $3^{rd}$ Ed., Method 2.5.5—Peroxide Value).

As used herein, the term "pharmaceutically acceptable carrier" refers to any formulation which is safe, and provides the appropriate delivery of an effective amount of one or more compounds of formula (1) for the prevention, treatment or amelioration of the disease or disorder targeted.

As used herein, the term "pharmaceutically effective amount" refers to an amount of one or more compounds of formula (I) that, when administered to a patient, prevents, treats or ameliorates a disease or disorder, or conditions associated thereof. As used herein, "an ophthalmically effective amount" refers to an amount of one or more compounds of formula (I) that, when administered to a patient, prevents, treats or ameliorates an ophthalmic disease or disorder, or conditions associated thereof. For the treatment of dry eye, such an effective amount will stimulate secretion of mucin in the eye and thus eliminate or improve dry eye conditions when administered to the eye. As used herein, "an effective amount to treat dry eye" refers to an amount of one or more compounds of formula (I) that, when administered to a patient, prevents, treats or ameliorates a dry eye disease or disorder, or conditions associated thereof. Generally, the compounds of formula (I) will be contained in a composition of the present invention in a concentration range of about 0.00001 to 10 per cent weight/volume ("% w/v"). Preferred ophthalmic, including dry eye-treatment, compositions will contain one or more compounds of formula (I) in a concentration of from about 0.00001–0.01% w/v.

The present invention is particularly directed to compositions useful in treating dry eye. Preferably, such compositions will be formulated as solutions, suspensions and other dosage forms for topical administration. Aqueous solutions are generally preferred, based on ease of formulation, biological compatibility (especially in view of the malady to be treated, e.g., dry eye-type diseases and disorders), as well as a patient's ability to easily administer such compositions by means of instilling one to two drops of the solutions in the affected eyes. However, the compositions may also be suspensions, viscous or semi-viscous gels, or other types of solid or semi-solid compositions. Suspensions may be preferred for compounds of formula (I) which are less soluble in water.

Preferably, the ophthalmic compositions of the present invention will also contain ethanol. As used herein, "an effective concentration of ethanol" refers to a concentration that enhances the biological efficacy of the formula (I) compositions in vivo. In general, the concentration of ethanol necessary for the enhancement of the compounds of formula (I) is believed to be somewhat proportional to the concentration of the formula (I) compound(s) administered. If a relatively high concentration of formula (I) compound (s), e.g., above 0.1% w/v, is administered, the concentration of ethanol in such compositions may be proportionally less than analogous compositions containing lower concentrations of formula (I) compounds. In general, however, the ethanol concentration contained in the ophthalmic compositions of the present invention will range from about 0.001–2% w/v. Compositions containing formula (I) concentrations of about 0.00001–0.05% w/v preferably will contain ethanol in a concentration of about 0.005–0.40% w/v, and most preferably, about 0.02–0.20% w/v.

Preferably, the compositions of the present invention will also contain a surfactant. Various surfactants useful in pharmaceutical formulations may be employed. The surfactant(s) may provide additional chemical stabilization of the formula (I) compounds and may further provide for the physical stability of the compounds. In other words, the surfactants may aid in preventing chemical degradation of the compounds of formula (I) and also prevent the compounds from binding to the containers in which their compositions are packaged. As used herein, "an effective concentration of surfactant(s)" refers to a concentration that enhances the chemical and physical stability of formula (I) compound(s). Examples of surfactants include, but are not limited to: Cremophor® EL, polyoxyl 20 ceto stearyl ether, polyoxyl 40 hydrogenated castor oil, polyoxyl 23 lauryl ether and poloxamers, e.g., poloxamer 407, may be used in the compositions. A preferred surfactant is polyoxyl 40 stearate. The concentration of surfactant will vary, depending on the concentration of formula (I) compound(s) and optional ethanol present in the formulation. In general, however, the surfactant(s) concentration will be about 0.001 to 2.0% w/v. Preferred compositions of the present invention will contain about 0.1% w/v of polyoxyl 40 stearate.

The compositions of the present invention may also include various other ingredients, such as tonicity agents, buffers, preservatives, co-solvents and viscosity building agents.

Various tonicity agents may be employed to adjust the tonicity of the composition, preferably to that of natural tears for ophthalmic compositions. For example, sodium chloride, potassium chloride, magnesium chloride, calcium chloride, dextrose and/or mannitol may be added to the composition to approximate physiological tonicity. Such an amount of tonicity agent will vary, depending on the particular agent to be added. In general, however, the compositions will have a tonicity agent concentration of about 0.1–1.5% w/v. Sodium chloride in the amount of 0.75% w/v is preferred.

An appropriate buffer system (e.g., sodium phosphate, sodium acetate, sodium citrate, sodium borate or boric acid) may be added to the compositions to prevent pH drift under storage conditions. The particular concentration will vary, depending on the agent employed. In general, however, such a concentration will range from about 0.02 to 2.0% w/v.

Antioxidants may be added to compositions of the present invention to protect the formula (I) compounds from oxidation during storage. Examples of such antioxidants include, but are not limited to, vitamin E and analogs thereof, ascorbic acid and derivatives, and butylated hydroxyanisole (BHA).

Compositions formulated for the treatment of dry eye-type diseases and disorders may also comprise aqueous carriers designed to provide additional, immediate, short-term relief of dry eye-type conditions. Such carriers can be formulated as a phospholipid carrier or an artificial tears carrier, or mixtures of both. As used in this paragraph and the immediately succeeding paragraph, the term "phospholipid" refers only to the phospholipids of the phospholipid carrier and does not refer to a compound of formula (I). As used herein, "phospholipid carrier" and "artificial tears carrier" refer to aqueous compositions which: (i) comprise one or more phospholipids (in the case of phospholipid carriers) or other compounds, which lubricate, "wet," approximate the consistency of endogenous tears, aid in natural tear build-up, or otherwise provide temporary relief of dry eye symptoms and conditions upon ocular administration; (ii) are safe; and (iii) provide the appropriate delivery vehicle for the topical administration of an effective amount of one or more compounds of formula (I). Examples or artificial tears compositions useful as artificial tears carriers include, but are not limited to, commercial products, such as Tears Naturale®, Tears Naturale II®, Tears Naturale Free®, and Bion Tears® (Alcon Laboratories, Inc., Fort Worth, Tex.). Examples of phospholipid carrier formulations include those disclosed in U.S. Pat. No. 4,804,539 (Guo et al.), U.S. Pat. No. 4,883,658 (Holly), U.S. Pat. No. 4,914,088 (Glonek), U.S. Pat. No. 5,075,104 (Gressel et al.), U.S. Pat. No. 5,278,151 (Korb et al.), U.S. Pat. No. 5,294,607 (Glonek et al.), U.S. Pat. No. 5,371,108 (Korb et al.), U.S. Pat. No. 5,578,586 (Glonek et al.); the foregoing patents are incorporated herein by reference to the extent they disclose phospholipid compositions useful as phospholipid carriers of the present invention.

The phospholipids useful in the phospholipid carriers are any natural or synthetic phospholipid compound comprising a glycerol-phosphoric acid ester or sphingomyelin backbone. Examples of glycerol-based phospholipid carriers useful in the present invention include those of the formula:

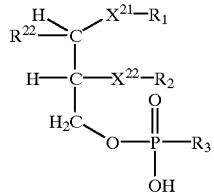

wherein, $X^{21}$ and $X^{22}$ are the same or different and are O, NH(C=O), O(C=O), or a direct bond;

$R^{22}$ is H or Ch=CH(CH$_2$)$_{12}$CH$_3$;

$X^{21}$-$R^1$ is OH, or $R^1$ is $C_{12-26}$ substituted or unsubstituted alkyl or alkenyl;

$R^2$ is $C_{12-26}$ substituted or unsubstituted alkyl or alkenyl; and $R^3$ is H, OH, OCH$_2$CH(NH$_3^+$)COO$^-$, OCH$_2$CH$_2$NH$_3$+, OCH$_2$CH$_2$N$^+$(CH$_3$)$_3$, OCH$_2$CH(OH)CH$_2$OH and O-inositol.

The phospholipids may be present as racemic or non-racemic compounds. Preferred glycerol based phospholipids are those wherein $X^{21}$-$R^1$ and/or $X^{22}$-$R^2$ comprise fatty acid esters or amides. Natural fatty acids are saturated, monounsaturated or polyunsaturated. Examples of fatty acid residues include, but are not limited to, laurate, myristate, palmitate, palmitoleate, stearate, oleate, linoleate, linolenate, eicosanoate, docosanoate and lignocerate. Preferred phospholipid types are the phosphatidylethanolamines, phosphatidylcholines, phosphatidylserines, phospatidylinositols and sphingomyelins. Examples of specific phospholipids include: 1,2-dipalmitoyl phosphatidyl choline ("DPPC") 1,2-dipalmityl phosphatidyl glycerol ("DPPG"), N-stearyl sphingomyelin, N-palmityl sphingomyelin, N-oleyl sphingomyelin, 1,2-distearoyl phosphatidyl ethanolamine ("DSPE"), 1,2-distearoyl phosphatidyl inositol ("DSPI"), 1-stearoyl-2-palmitoyl phosphatidyl ethanolamine ("SPPE"), 1-stearoyl-2-palmitoyl phosphatidyl choline ("SPPC"), 1,2-dipalmitoyl phosphatidyl ethanolamine ("DPPE"), 1,2-dioleoyl phophatidyl ethanolamine ("DOPE"), 1,2-dioleoyl phophatidyl serine ("DOPS"), and 1,2-dipalmitoyl phosphatidyl serine ("DPPS"). The most preferred phospholipid carriers are the phosphatidylethanolamines and sphingomyelins. Phospholipids are available from a variety of natural sources and may be synthesized by methods known in the art; see, for example, Tsai et. al., *Biochemistry*, volume 27, page 4619 (1988); and Dennis et. al., *Biochemistry*, volume 32, page 10185 (1993).

Other compounds designed to lubricate, "wet," approximate the consistency of endogenous tears, aid in natural tear build-up, or otherwise provide temporary relief of dry eye symptoms and conditions upon ocular administration the eye are known in the art. Such compounds may enhance the viscosity of the composition, and include, but are not limited to: monomeric polyols, such as, glycerol, propylene glycol, ethylene glycol; polymeric polyols, such as, polyethylene glycol, hydroxypropylmethyl cellulose ("HPMC"), carboxy methylcellulose sodium, hydroxy propylcellulose ("HPC"), dextrans, such as, dextran 70; water soluble proteins, such as gelatin; and vinyl polymers, such as, polyvinyl alcohol, polyvinylpyrrolidone, povidone and carbomers, such as, carbomer 934P, carbomer 941, carbomer 940, carbomer 974P.

Other compounds may also be added to the ophthalmic compositions of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers. In general, the phospholipid carrier or artificial tears carrier compositions will exhibit a viscosity of 1 to 400 centipoises ("cps"). Preferred compositions containing artificial tears or phospholipid carriers will exhibit a viscosity of about 25 cps.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

The preferred compositions of the present invention are intended for administration to a human patient suffering from dry eye or symptoms of dry eye. Preferably, such compositions will be administered topically. In general, the doses used for the above described purposes will vary, but will be in an effective amount to provide immediate, short-term dry eye relief, and to increase mucin production in the eye and thus eliminate or improve the dry eye condition of the patient. Generally, 1–2 drops of such compositions will be administered 1–10 times per day for the treatment of dry eye or other ocular disease or disorder. Preferably, 1–2 drops of the compositions will be administered 1–4 times per day.

The present invention is also directed to stable, stock compositions comprising one or more compounds of formula (I) and ethanol. The inventors believe that storing the compounds of formula (I) in an ethanolic solution provides greater stability of the compounds of formula (I) over analogous aqueous compositions, or neat compounds of formula (I) compositions. Such compositions comprise one or more compounds of formula (I) and an amount of ethanol to solubilize the compounds of formula (I) in solution. Preferably, the ethanolic stock solutions will contain anhydrous ethanol, but aqueous ethanolic solutions are also contemplated by the present invention. Generally, the stock solutions will contain ethanol in a concentration of about 25 to 100 % volume/volume ("v/v"). Typically, such stock solutions will contain compounds of formula (I) in a high concentration relative to the pharmaceutical compositions of the present invention.

The following example illustrates a composition of the present invention. The actual pH of the composition may vary (e.g., between 6–8), and the concentrations of the various ingredients included in the exemplified composition may vary, but are included in the compositions in the approximate amounts shown.

EXAMPLE 1

| Ingredient | Amount (% w/v) |
| --- | --- |
| Compound of Formula I | 0.00001–0.05 |
| Ethanol | 0.0505 |
| Polyoxyl 40 Stearate | 0.1 |
| Boric Acid | 0.25 |
| Sodium Chloride | 0.75 |
| Disodium Edetate | 0.01 |
| Polyquaternium-1 | 0.001 |
| NaOH/HCl | q.s., pH = 7.5 |
| Purified Water | q.s. 100% |

The above composition is prepared by the following method. The batch quantities of polyoxyl 40 stearate, boric acid, sodium chloride, disodium edetate, and polyquaternium-1 are weighed and dissolved by stirring in 90% of the batch quantity of purified water. The pH is adjusted to 7.5±0.1 with NaOH and/or HCl. Under yellow light or reduced lighting, the batch quantity of the compound of Formula I as a stock solution in ethanol and the additional quantity of ethanol necessary for the batch are measured and added. Purified water is added to q.s. to 100%. The mixture is stirred for five minutes to homogenize and then filtered through a sterilizing filter membrane into a sterile recipient.

Preferably, the above process is performed using glass, plastic or other non-metallic containers or containers lined with such materials.

The invention in its broader aspects is not limited to the specific details shown and described above. Departures may be made from such details within the scope of the accompanying claims without departing from the principles of the invention and without sacrificing its advantages.

What is claimed is:

1. A composition for the treatment of dry eye and other disorders requiring the wetting of the eye comprising a pharmaceutically acceptable carrier and a pharmaceutically effective amount of one or more compounds of the following formula I:

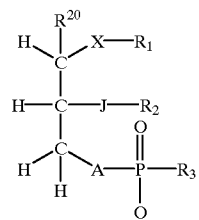

(I)

wherein:

$R^{20}$ is H or Ch=CH(CH$_2$)$_{12}$CH$_3$;

X is O or S;

$R^1$ is H, (C=O)R4 or CH$_2$R$^4$;

J is O or NH;

$R^2$ is (C=O)R$^5$;

A is CH$_2$ or O;

$R^3$ is OCH$_2$CH(NH$_3^+$)COO$^-$, OCH$_2$CH$_2$NH$_3$+, OCH$_2$CH$_2$N$^+$(CH$_3$)$_3$, OCH$_2$CH(OH)CH$_2$OH, O-inositol, OH, H, or alkyl;

$R^4$ and $R^5$ are independently a HETE derivative; substituted or unsubstituted C$_{12-30}$ alkyl or alkenyl (the alkenyl group containing one or more double bonds); alkyl(cycloalkyl)alkyl; alkyl(cycloalkyl); alkyl (heteroaryl); alkyl(heteroaryl)alkyl; or alkyl-M-Q; wherein the substitution is alkyl, halo, hydroxy, or functionally modified hydroxy; wherein:

M is O or S; and

Q is H, alkyl, alkyl(cycloalkyl)alkyl, alkyl(cycloalkyl), alkyl(heteroaryl) or alkyl(heteroaryl)alkyl;

with the proviso that at least one of $R^4$ and $R^5$ must be a HETE derivative;

wherein the HETE derivative is a structural fragment of formula II:

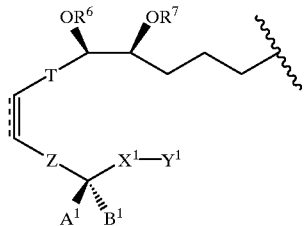

II wherein:

OR$^6$ and OR$^7$ are the same or different and comprise a free or functionally modified hydroxy group;

T and Z are the same or different and are CH$_2$CH$_2$, cis- or trans-CH=CH, or C≡C;

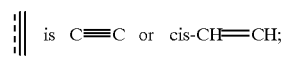

one of A$^1$, B$^1$ is H or CH$_3$, and the other is a free or functionally modified hydroxy group, or A$^1$–B$^1$ comprises a double bonded oxygen as a carbonyl, or A$^1$–B$^1$ is OCH$_2$CH$_2$O;

$X^1$ is CR$^{16}$R$^{17}$(CH$_2$)$_q$ or CR$^{16}$R$^{17}$(CH$_2$)$_q$O, with q is 0–6;

$R^{16}$ and $R^{17}$ are the same or different and are H or CH$_3$;

$Y^1$ is $CH_3$ or a phenyl ring optionally substituted with alkyl, halo, trihalomethyl, acyl, or a free or functionally modified hydroxy, thiol, or amino group;

or $X^1$-$Y^1$ is $(CH_2)_p Y^{20}$, p is 0–6,

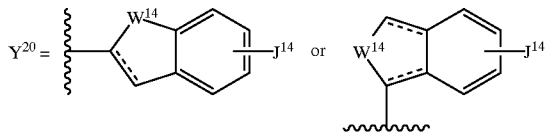

wherein:

$W^{14}$ is $CH_2$, O, $S(O)_m$, $NR^{21}$, $CH_2CH_2$, Ch=CH, $CH_2O$, $CH_2S(O)_m$, Ch=N, or $CH_2NR^{21}$;

m is 0–2;

$NR^{21}$ is NH or a functionally modified amino group;

$J^{14}$ is H, alkyl, acyl, halo, trihalomethyl, or a free or functionalized hydroxy, thiol, or amino group; and — is a single or double bond;

or $X^1$-$Y^1$ is cyclohexyl; and the wavy line indicates the point of attachment.

2. The composition of claim 1, wherein for the compound of formula I:

X is O;

$R^1$ is H or (C=O)$R^4$;

A is O;

$R^3$ is $OCH_2CH(NH_3^+)COO^-$, $OCH_2CH_2NH_3+$, $OCH_2CH_2N^{30}$ $(CH_3)_3$, O-inositol, or OH; and $R^5$ is a HETE derivative.

3. The composition of claim 1, wherein the composition is a topical ophthalmic formulation.

4. A method for the treatment of dry eye and other disorders requiring the wetting of the eye which comprises administering to a mammal a composition comprising a pharmaceutically acceptable carrier and a pharmaceutically effective amount of one or more compounds of the following formula I:

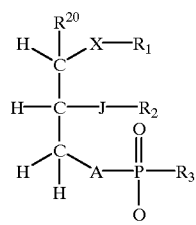
(I)

wherein:

$R^{20}$ is H or Ch=CH$(CH_2)_{12}CH_3$;

X is O or S;

$R^1$ is H, (C=O)R4 or $CH_2R^4$;

J is O or NH;

$R^2$ is (C=O)$R^5$;

A is $CH_2$ or O;

$R^3$ is $OCH_2CH(NH_3^+)COO^-$, $OCH_2CH_2NH_3+$, $OCH_2CH_2N^+(CH_3)_3$, $OCH_2CH(OH)CH_2OH$, O-inositol, OH, H, or alkyl;

$R^4$ and $R^5$ are independently a HETE derivative; substituted or unsubstituted $C_{12-30}$ alkyl or alkenyl (the alkenyl group containing one or more double bonds); alkyl(cycloalkyl)alkyl; alkyl(cycloalkyl); alkyl (heteroaryl); alkyl(heteroaryl)alkyl; or alkyl-M-Q; wherein the substitution is alkyl, halo, hydroxy, or functionally modified hydroxy; wherein:

M is O or S; and

Q is H, alkyl, alkyl(cycloalkyl)alkyl, alkyl(cycloalkyl), alkyl(heteroaryl) or alkyl(heteroaryl)alkyl;

with the proviso that at least one of $R^4$ and $R^5$ must be a HETE derivative;

wherein the HETE derivative is a structural fragment of formula II:

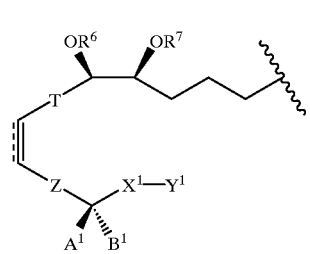
II wherein:

$OR^6$ and $OR^7$ are the same or different and comprise a free or functionally modified hydroxy group;

T and Z are the same or different and are $CH_2CH_2$, cis- or trans-CH=CH, or C≡C;

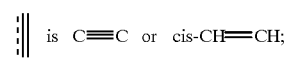
is C≡C or cis-CH=CH;

one of $A^1$, $B^1$ is H or $CH_3$, and the other is a free or functionally modified hydroxy group, or $A^1$-$B^1$ comprises a double bonded oxygen as a carbonyl, or $A^1$-$B^1$ is $OCH_2CH_2O$;

$X^1$ is $CR^{16}R^{17}(CH_2)_q$ or $CR^{16}R^{17}(CH_2)_qO$, with q is 0–6;

$R^{16}$ and $R^{17}$ are the same or different and are H or $CH_3$;

$Y^1$ is $CH_3$, or a phenyl ring optionally substituted with alkyl, halo, trihalomethyl, acyl, or a free or functionally modified hydroxy, thiol, or amino group;

or $X^1$-$Y^1$ is $(CH_2)_p Y^{20}$, p is 0–6,

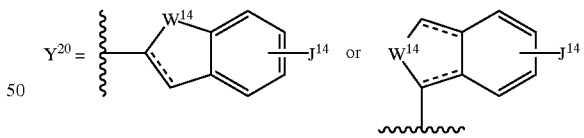

wherein:

$W^{14}$ is $CH_2$, O, $S(O)_m$, $NR^{21}$, $CH_2CH_2$, Ch=CH, $CH_2O$, $CH_2S(O)_m$, Ch=N, or $CH_2NR^{21}$;

m is 0–2;

$NR^{21}$ is NH or a functionally modified amino group;

$J^{14}$ is H, alkyl, acyl, halo, trihalomethyl, or a free or functionalized hydroxy, thiol, or amino group; and — is a single or double bond;

or $X^1$–$Y^1$ is cyclohexyl; and the wavy line indicates the point of attachment.

5. The method of claim 4, wherein the composition is administered topically.

6. The method of claim 4, wherein for the compound of formula I:

X is O;

$R^1$ is H or (C=O)$R^4$;

A is O;

$R^3$ is OCH$_2$CH(NH$_3^+$)COO$^-$, OCH$_2$CH$_2$NH$_3$+, OCH$_2$CH$_2$N$^+$(CH$_3$)$_3$, O-inositol, or OH; and $R^5$ is a HETE derivative.

7. A compound of formula I:

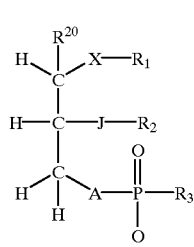

(I)

wherein:

$R^{20}$ is H or Ch=CH(CH$_2$)$_{12}$CH$_3$,

X is O or S;

$R^1$ is H, (C=O)R4 or CH$_2$R$^4$;

J is O or NH;

$R^2$ is (C=O)$R^5$;

A is CH$_2$ or O;

$R^3$ is OCH$_2$CH(NH$_3^+$)COO$^-$, OCH$_2$CH$_2$NH$_3$+, OCH$_2$CH$_2$N$^+$(CH$_3$)$_3$, OCH$_2$CH(OH)CH$_2$OH, O-inositol, OH, H, or alkyl;

$R^4$ and $R^5$ are independently a HETE derivative; substituted or unsubstituted C$_{12-30}$ alkyl or alkenyl (the alkenyl group containing one or more double bonds); alkyl(cycloalkyl)alkyl; alkyl(cycloalkyl); alkyl (heteroaryl); alkyl(heteroaryl)alkyl; or alkyl-M-Q; wherein the substitution is alkyl, halo, hydroxy, or functionally modified hydroxy; wherein:

M is O or S; and

Q is H, alkyl, alkyl(cycloalkyl)alkyl, alkyl(cycloalkyl), alkyl(heteroaryl) or alkyl(heteroaryl)alkyl;

with the proviso that at least one of $R^4$ and $R^5$ must be a HETE derivative;

wherein the HETE derivative is a structural fragment of formula II:

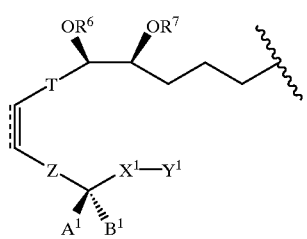

II wherein:

OR$^6$ and OR$^7$ are the same or different and comprise a free or functionally modified hydroxy group;

T and Z are the same or different and are CH$_2$CH$_2$, cis- or trans-CH=CH, or C≡C;

┊┊┊ is C≡C or cis-CH=CH;

one of A$^1$, B$^1$ is H or CH$_3$, and the other is a free or functionally modified hydroxy group, or A$^1$-B$^1$ comprises a double bonded oxygen as a carbonyl, or A$^1$-B$^1$ is OCH$_2$CH$_2$O;

X$^1$ is CR$^{16}$R$^{17}$(CH$_2$)$_q$ or CR$^{16}$R$^{17}$(CH$_2$)$_q$O, with q is 0–6;

R$^{16}$ and R$^{17}$ are the same or different and are H or CH$_3$;

Y$^1$ is CH$_3$ or a phenyl ring optionally substituted with alkyl, halo, trihalomethyl, acyl, or a free or functionally modified hydroxy, thiol, or amino group;

or X$^1$-Y$^1$ is (CH$_2$)$_p$Y$^{20}$, p is 0–6,

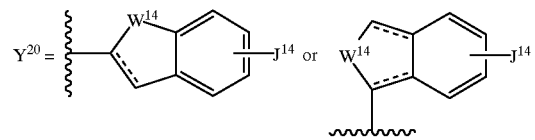

wherein:

W$^{14}$ is CH$_2$, O, S(O)$_m$, NR$^{21}$, CH$_2$CH$_2$, Ch=CH, CH$_2$O, CH$_2$S(O)$_m$, CH=N, or CH$_2$NR$^{21}$;

m is 0–2;

NR$^{21}$ is NH or a functionally modified amino group;

J$^{14}$ is H, alkyl, acyl, halo, trihalomethyl, or a free or functionalized hydroxy, thiol, or amino group; and — is a single or double bond;

or X$^1$–Y$^1$ is cyclohexyl; and the wavy line indicates the point of attachment.

8. The compound of claim 7, wherein:

X is O;

$R^1$ is H or (C=O)$R^4$;

A is O;

$R^3$ is OCH$_2$CH(NH$_3^+$)COO$^-$, OCH$_2$CH$_2$NH$_3$+, OCH$_2$CH$_2$N$^+$(CH$_3$)$_3$, O-inositol, or OH; and $R^5$ is a HETE derivative.

* * * * *